United States Patent [19]

Louderback et al.

[11] 4,324,687
[45] Apr. 13, 1982

[54] BLOOD BIOCHEMISTRY CONTROL STANDARD

[76] Inventors: Allan L. Louderback, 9661 Longden Ave., Temple City, Calif. 91780; Paul R. Szatkowski, 24 Winthrop Rd., Bethel, Conn. 06801

[21] Appl. No.: 162,065

[22] Filed: Jun. 23, 1980

Related U.S. Application Data

[63] Continuation-in-part of Ser. No. 12,849, Feb. 15, 1979, abandoned.

[51] Int. Cl.³ .................. G01N 33/48; C09K 3/00
[52] U.S. Cl. .................. 252/408; 23/230 B; 23/901; 23/902; 23/905; 23/908; 23/913; 23/916; 424/2; 424/3; 435/2; 435/4; 435/16; 435/17; 435/21; 435/22; 435/26
[58] Field of Search .................. 252/408; 23/230 B; 435/4, 21, 17, 22, 26, 16, 2, 183; 424/2, 3

[56] References Cited

U.S. PATENT DOCUMENTS

| | | | |
|---|---|---|---|
| 3,558,522 | 1/1971 | Louderback et al. | 252/408 |
| 3,682,835 | 8/1972 | Louderback | 252/408 |
| 3,728,226 | 4/1973 | Louderback | 252/408 |
| 3,873,467 | 3/1975 | Hunt | 252/408 |
| 3,973,913 | 8/1976 | Louderback | 252/408 |
| 3,977,995 | 8/1976 | Louderback et al. | 252/408 |
| 4,020,006 | 4/1977 | Parker | 252/408 |
| 4,102,810 | 7/1978 | Armstrong | 252/408 |
| 4,126,575 | 11/1978 | Louderback et al. | 252/408 |
| 4,189,401 | 2/1980 | Louderback | 252/408 |
| 4,199,471 | 4/1980 | Louderback et al. | 252/408 |

FOREIGN PATENT DOCUMENTS

1509539 5/1978 United Kingdom ............ 252/408

*Primary Examiner*—Teddy S. Gron

[57] ABSTRACT

A blood biochemistry control standard for the quality control of the analytical measurement of blood biochemistry components is disclosed. The control standard comprises an aqueous suspension of red blood cells which have been stabilized by mild treatment with aldehyde and saline and then slowly equilibrated with at least one additionally incorporated non-gaseous biochemical analyte in a concentration of clinical significance.

4 Claims, No Drawings

BLOOD BIOCHEMISTRY CONTROL STANDARD

CROSS-REFERENCE TO RELATED APPLICATION

This is a continuation-in-part of application Ser. No. 12,849, filed Feb. 15, 1979, now abandoned.

BACKGROUND OF THE INVENTION

This invention relates to a stable blood biochemistry control standard.

The determination of various blood serum components is now routine practice in the clinical diagnosis of disease. A wide variety of instruments has been developed for the rapid analysis of these blood serum components. Most of the instruments employ colorimetry and UV spectrophotometry as the means of the analysis.

In conjunction with the performance of the analytical tests made by these instruments, so-called biochemistry control standards are employed for control of the instrument to ensure constant standardization of the various biochemical determinations. Illustrative examples of such biochemistry control standards are those described in U.S. Pat. Nos. 3,466,249; 3,682,835; and 3,728,226. These prior art biochemistry control standards typically comprise aqueous blood serum, or freeze-dried serum which can be reconstituted with water before use, in which the serum has been treated by one means or another to provide certain desired properties.

Recently, new instruments have been developed which can utilize whole blood samples for analysis and are not limited to use of merely the blood serum fraction. When utilizing these instruments for biochemical determinations, the patient's blood samples need not be spun down to remove the cells and it is unnecessary to first wait for the plasma to clot before separating the serum therefrom. Thus, these instruments employ electrode systems which are not adversely affected by any blood cells present in the sample or even by hemolysis in the millieu surrounding the cells.

For use in the control of such instruments, it would be desirable to have a control standard which more nearly resembles the patient's whole blood, including the red cells, rather than the serum based biochemistry control standards of the prior art. Use of normal whole blood itself, of course, is too variable and unstable since normal red cells lyse and release enzymes, hemoglobin and $K^+$ into the millieu.

DESCRIPTION OF THE INVENTION

In accordance with the present invention, a stable blood biochemistry standard is provided in which red cells are stabilized by mild treatment with aldehyde and saline and then slowly equilibrated with a solution of at least one additionally incorporated non-gaseous biochemical analyte in a concentration established by instrumentation parameters and clinical significance.

As used herein, the term "analyte" refers to any blood electrolyte, ion, molecule or other blood component which is desired to be determined in conjunction with conventional blood biochemistry analysis. The concentration of the analyte is conveniently defined as equal to the weight of the analyte in a prescribed volume such as, e.g., mg/ml, gm/dl or $\mu$gm/dl. The weight may be offset to its molar concentration whereby the concentration may be defined in terms of meq/l or mmol/l.

By way of illustration and not limitation, the following substances are specific examples of analytes which can be equilibrated with the aldehyde stabilized red cells in accordance with the invention:

Sodium
Potassium
Lithium
Magnesium
Calcium
Phosphorus
Iron
Chloride
Bicarbonate
Blood urea nitrogen (BUN)
Creatinine
Uric acid
Bilirubin
Glucose
Cholesterol
Triglycerides
Protein bound iodine (PBI)
Acid phosphatase
Alkaline phosphatase
Amylase
Lactate dehydrogenase (LDH)
Creatine phosphokinase (CPK)
Serum glutamic oxalacetic transaminase (SGOT)
Serum glutamic pyruvic transaminase (SGPT)

Other analytes which can be used in this invention can be readily determined by the person skilled in the art after reading this disclosure by reference to text books on clinical chemistry such as, e.g., Tietz, "Fundamentals of Clinical Chemistry", W. B. Saunders Company, Philadelphia, Pa., (2d ed. 1976); Davidson & Henry, "Todd-Sanford Clinical Diagnosis By Laboratory Methods", W. B. Saunders Company (15th ed. 1974).

The red cells which are equilibrated with the analytes are specially treated aldehyde stabilized red cells. This special treatment is essential since the untreated cells can not be equilibrated with the analytes without swelling and breaking open due to the normal tendency of the cells to maintain a specific physiological millieu within the cells. Although aldehyde treatment of red cells for blood gas control standards is known as can be seen from U.S. Pat. Nos. 3,973,913 and 4,126,575, it has not heretofore been known to equilibrate these red cells with various analytes for the preparation of a blood biochemistry control standard as defined herein. In said prior patents the aldehyde stabilized red cells are saturated with blood gases and blood gas-forming components as needed for the determination of blood gases such as oxygen, carbon dioxide and carbon monoxide. These prior art blood gas control standards are adapted for the determination of gases associated with the respiratory system, e.g., $O_2$ and $CO_2$, or the toxic gas CO. The instruments adapted for the determination of these gases are equipped with various electrodes for directly measuring the blood gases in the sample. As an example, in the determination of blood $CO_2$, the $CO_2$ gas will pass through a semi-permeable membrane and alter the pH of a buffer inside the $CO_2$-measuring electrode. By way of distinction, in the present invention the analysis of the sample comprises a biochemical determination of a non-gaseous component of blood such as, e.g., an electrolyte or ionic constituent. As such, the blood biochemistry control standard of this invention has a significantly different composition than the blood gas control standards of the prior art.

Although the blood gas standards of the prior art may contain small amounts of certain ionic constituents such as, e.g., $Na^+$, $K^+$, citrate or bicarbonate ions, these constituents are not incorporated in the blood gas control standards in the same levels as required for clinical significance for the purpose of human diagnosis as desired herein. Thus, any bicarbonate added to the prior art blood gas control standard is for the purpose of providing a desired level of mm Hg pressure such as to establish a stated $pCO_2$ level. In the present blood biochemistry control standard, bicarbonate or other such substances are not added in such levels or combinations to provide a gaseous component. However, bicarbonate ion when used in the present invention is employed such as to provide a given level of meq/l to establish a level of clinical significance for the diagnosis of bicarbonate ion in the blood. Moreover, any saline used in the prior art blood gas control standards is to provide an isotonic medium and citrate is used merely as an anticoagulant.

In accordance with the present invention, the aldehyde stabilized red cells are slowly equilibrated with the analytes by gradual incorporation therein from a biochemical wash solution in the desired concentrations. The cells are thus washed with this solution over a period of at least about five minutes but preferably about ten minutes at ambient temperature to ensure the appropriate slow and gradual equilibration. Longer washing periods, e.g., up to about one hour or greater can be used but are unnecessary. It is essential to conduct this equilibration after, rather than before, the treatment with aldehyde. Attempts to equilibrate the red cells prior to the stabilization with aldehyde cause the red cells to swell and break open as already stated above.

The red cells to be treated with aldehyde can be fresh or outdated cells (cells stored in excess of the normal 21–28 day storage). These cells are preferably human red cells although red cells of other animal species also can be used such as, e.g., bovine, equine, porcine and sheep species.

In order to ensure appropriate stabilization with aldehyde, the red cells are first carefully separated from the other blood components by thoroughly washing in saline solution. The washed red cells are then mildly admixed with a solution of aldehyde and saline. It is important in this step to avoid rigorous and prolonged treatment such as with tannic acid or elevated temperatures which are used by the prior art to prepare hard, stabilized red cells which do not even lyse in sterilized water. Following this mild treatment with aldehyde and saline, the cells are again thoroughly washed in saline solution to remove residual aldehyde prior to equilibration with the desired analytes.

Aldehydes which can be used in the aldehyde/saline solution generally are aliphatic aldehydes having from one to about six carbon atoms such as, for example, formaldehyde, acetaldehyde, propionaldehyde, butyraldehyde, malonic aldehyde, succinaldehyde, glutaraldehyde and pyruvic aldehyde. The saline preferably is normal physiological saline and the aldehyde preferably is formaldehyde.

The aldehyde preferably ranges from about 0.1 to about 0.6 molar aldehyde in saline. An especially preferred treatment solution can be made by admixing about 40 ml of formaldehyde (37% solution) with 500 ml of normal physiological saline and then admixing this treatment solution with the red cells suspended in another 2000 ml of saline. This will provide an overall 0.16 molar formaldehyde in 0.9% NaCl solution.

The mild treatment with the aldehyde/saline solution is carried out by slow addition to the blood cell suspension in saline, preferably over a 5–10 minute period with stirring at ambient temperature (ca. 20°–25° C.). The stirring of the suspension of the red cells in the aldehyde/saline solution is then continued for a total stirring time of about 15 minutes to about six hours. About 30 minutes is preferred. During this treatment the red cells assume a brilliant red color as the hemoglobin is converted to about 100% oxyhemoglobin.

The saline washing of the red cells, both before and after the aldehyde treatment, can be carried out by washing with from about 2 to about 30 volumes of saline per one volume of red cells. The biochemical wash solution also can be used in proportions of about 2 to about 30 volumes of solution per volume of red cells. Greater dilutions are unnecessary. Preferably, the red cells from one unit of whole blood (one pint) are washed with about 2 to 4 liters of saline in each saline washing and 2 to 4 liters of biochemical wash solution.

The separation of the red cells from the other blood components and the washings with saline and aldehyde/saline solutions can be conveniently carried out in continuous flow type centrifuges such as commercially available from the Haemonetics Corp. Centrifuges of this type are described, for example, in U.S. Pat. No. 3,706,412. In this type of centrifuge, the bowl has two parts, one that rotates and another that is stationary. As the blood or separated red cells enter the spinning bowl, the cells are gently distributed to the periphery and as the bowl fills, the supernatant separates from the red cells. The red cells are held in suspension by centrifugal force while the supernatant is expelled through an effluent port into a waste collection receptacle.

The washing solution is then made to follow the same path as the red cells. The geometry of the centrifuge keeps the cells circulating against the flow of fresh wash solution as the used wash solution is expelled through the effluent port. When the washing is complete, the centrifuge is stopped and the washed red cells are siphoned into a separate collection vessel.

Another example of a conventional blood separation centrifuge that is suitable for use in the invention is the Celltrifuge separator which is commercially available from the American Instrument Company.

Various minor additives can also be employed in the wash solutions or otherwise added to the final product to impart certain desired additional properties to the treated red cells. For example, small but effective amounts of antibiotics and antifungals can be used for their respective protective effects. Thus, it is preferred to incorporate minor amounts of neomycin and chloramphenicol antibiotics and Fungizone antifungal into the wash solution. By way of illustration, use of about 330 mg neomycin, 990 mg chloramphenicol, and 10 mg Fungizone per three liters of the biochemical wash solution is eminently suitable.

Minor amounts of various stabilizers for enzymes, for example, gelatin, can also be employed in the blood biochemistry control standard when enzymes are included in the biochemical wash solution. Thus, use of about 50 to 1500 mg/dl and preferably about 750 ml/dl of gelatin in the wash solution can be used with excellent effect for enzyme stabilization.

In accordance with another aspect of the invention, the blood biochemistry control standard is placed in a proteinaceous environment by admixture with blood serum proteins, preferably to a concentration of from about 3 to about 9 gm/dl of protein. These proteins can be conveniently added to the control standard by incorporation from the biochemical wash solution. For example, blood serum can be concentrated by dialysis and ultrafiltration to a level of from about 14 to about 25 gm/dl of protein. The protein concentration can be reduced by admixture of the concentrated proteins with the biochemical wash solution in any desired proportions. For example, mixture of about equal parts of the concentrated protein solution and the biochemical wash solution will result in reducing the protein concentration by about one half. The biochemical wash solution is then used to wash the aldehyde treated red cells as before, and the final product will then have the serum proteins incorporated therein. The final product more closely resembles the patient's sample except that there is little or no hemolysis when the product is stored at about 2° to 8° C.

The following detailed examples will further illustrate the invention, although it will be appreciated that the invention is not limited to the details of these specific examples.

EXAMPLE 1

A unit (one pint) of fresh human blood collected in CPD or 4% citric acid anticoagulant solution is spun down in an ordinary centrifuge to separate the cells from the plasma. The plasma is retained for use in Example 2, below. The separated cells are expressed into a Haemonetics Corp. continuous flow centrifuge equipped with a 375 ml. bowl. The cells are distributed to the periphery and the supernatant is expelled through the effluent port. While spinning, the cells are washed with 2 to 3 liters of a washing solution comprising an aqueous solution of 0.9% NaCl (normal physiological saline). The washed cells are siphoned into a collection vessel and then transferred to a vessel which contains two liters of saline. To the red cells/saline suspension at 25° C. is then added slowly over a brief time period of 5 to 7 minutes a solution made up of 500 ml saline and 40 ml formaldehyde (37%) to thereby provide a 0.16 molar formaldehyde in 0.9% NaCl solution. The mixture is stirred for an additional 30 minutes, during which time the cells assume a bright red color resembling fresh arterial blood. The formaldehyde treated cell mixture is then transferred to the continuous flow centrifuge wherein the cells are further washed with 3 liters of 0.9% saline solution. The cells are gently held to an outer wall of the centrifuge bowl while the saline solution washes through the cells and removes the aldehyde from the cells in a gentle manner. The cells are then further washed in the same manner with 4 liters a biochemical wash solution made up to contain the following analytes in the range of concentrations shown:

| Analyte | Concentration |
| --- | --- |
| Sodium | 120 to 160 meq/l |
| Potassium | 2 to 9 meq/l |
| Urea (for BUN) | 10 to 130 mg/dl |
| | (4.6 to 60.6 mg/dl urea nitrogen) |

-continued

| Analyte | Concentration |
| --- | --- |
| Glucose | 25 to 500 mg/dl |
| Uric acid | 2 to 12 mg/dl |
| Chloride | 80 to 130 meq/l |
| Magnesium | 0.5 to 5 meq/l |
| Creatinine | 0.5 to 10 mg/dl |
| Phosphorus | 0.5 to 10 mg/dl |
| Calcium | 0.5 to 14 mg/dl |
| Bicarbonate | 3 to 40 meq/l |
| Iron | 25 to 300 ugm/dl |
| Lithium | 0.2 to 4 meq/l |
| Bilirubin | 0.5 to 30 mg/dl |

The washed cells are then siphoned off into a collection vessel and gently mixed and allowed to come into equilibrium with the analytes for a period of about 10 minutes with gentle stirring. Assay of the analytes and minor adjustments, if desired, can be made at this time. For example, enzymes can be assayed and additional enzymes can be added to raise the enzyme levels within the range of concentrations as follows:

| Enzyme | Concentration |
| --- | --- |
| LDH | 0-600 IU/l |
| CPK | 0-800 IU/l |
| SGOT | 0-150 IU/l |
| SGPT | 0-150 IU/l |
| Alk. phosphatase | 0-500 IU/l |
| Acid phosphatase | 0-30 IU/l |
| Amylase | 0-300 IU/l |

Enzyme assays should be made at 37° C. Following the assay of analytes and the making of minor adjustments to their concentration levels, the cell suspension is dispensed into bottles, vials or other suitable containers and then sealed and stored at 2° to 8° C. The product is stable for 2 to 6 months.

An example of an analytical instrument which can utilize the blood biochemical control standard of this invention is the Beckman ASTRA 4 and ASTRA 8 Automated Stat Routine Analyzer System which incorporates computer control and monitoring for testing of electrolytes and routine chemistries. It determines glucose by oxygen-rate sensing; blood urea nitrogen by rate conductivity; creatine by colorimetric method; Na and K by ion selective electrodes; chloride by colorimetric titration; and $CO_2$ by rate pH.

EXAMPLE 2

The plasma retained from Example 1, above, is clotted by addition of bovine thrombin (Parke Davis) and calcium. After alternate freezing and thawing 3 times, the clot is separated from the serum by centrifugation. The calcium level in the remaining serum is then reduced as follows: The serum is diluted by admixture with an equal volume of distilled water and then subjected to ultrafiltration in a Pellicon System (Millipore) equipped with a 10,000 molecular weight band pass ultrafilter. The serum is then concentrated to about 14% total protein per 100 ml (14 gm/dl). Alternatively, the serum can be concentrated to about 25% total protein. A biochemical wash solution is prepared as in accordance with Example 1, above, and thoroughly admixed with the foregoing concentrated serum in proportions such that when mixed with the aldehyde treated red cells the final product will have a preferred protein concentration of from about 3% to about 9% protein. This mixture of the concentrated serum in the biochemical wash solution is used in the same manner as the biochemical wash solution of Example 1, above, for washing into the aldehyde treated red cells. The final product is dispensed into containers and sealed and stored as in Example 1. This product can be used in the manner of the product of Example 1 for the control of analytical instruments which can utilize whole blood samples. It has the added advantage in that it can also be used with instruments which utilize blood serum samples whereby the blood control standard can be spun down to remove cells prior to application to the instrument. The product of this example therefore is a better control standard for the clinical laboratory from the standpoint of its greater versatility in application to various types of analytical instruments and since it more closely resembles the patient's sample than the product of Example 1.

Various other examples will be apparent to the person skilled in the art after reading the instant disclosure without departing from the spirit and scope of the invention and it is intended that all such examples be included within the scope of the appended claims.

What is claimed is:

1. A blood biochemistry control standard for the quality control of the analytical measurement of non-gaseous blood biochemistry components comprising an aqueous suspension of red blood cells which are (a) stabilized by mild treatment with aldehyde and saline at ambient temperature whereby said cells are lyseable in water and then (b) slowly and gradually equilibrated by washing over a period of at least about five minutes with an aqueous biochemical wash solution of at least one additionally incorporated non-gaseous biochemical analyte selected from the group consisting of the following analytes in the following concentrations of clinical diagnostic significance:

Sodium: 120 to 160 meq/l
   Potassium: 2 to 9 meq/l
   Urea: 10 to 130 mg/dl
   Glucose: 25 to 500 mg/dl
   Uric acid: 2 to 12 mg/dl
   Chloride: 80 to 130 meq/l
   Magnesium: 0.5 to 5 meq/l
   Creatinine: 0.5 to 10 mg/dl
   Phosphorus: 0.5 to 10 mg/dl
   Calcium: 0.5 to 14 mg/dl
   Bicarbonate: 3 to 40 meq/l
   Iron: 25 to 300 μgm/dl
   Lithium: 0.2 to 4 meq/l
   Bilirubin: 0.5 to 30 mg/dl.

2. The blood biochemistry control standard of claim 1 including additionally blood serum protein in an amount of from about 3% to about 9%.

3. The method of making the blood biochemistry control standard of claim 1 comprising thoroughly washing red blood cells in saline solution, mildly admixing with a solution of aldehyde and saline, thoroughly washing in saline solution to remove substantially all the residual aldehyde, slowly equilibrating by gentle washing with an aqueous solution of at least one additionally incorporated non-gaseous biochemical analyte in a concentration of clinical diagnostic significance and thereafter collecting the thus treated red cells in aqueous suspension in a sealed receptacle.

4. The method of claim 3 in which the biochemical wash solution contains additionally blood serum protein to a level such that after washing the red cells the concentration of serum protein in the control standard is from about 3% to about 9%.

* * * * *